United States Patent [19]

Röder et al.

[11] 4,416,983
[45] Nov. 22, 1983

[54] DETERMINATION OF NAD(P)H OR SALICYLATE

[75] Inventors: Albert Röder, Seeshaupt; Joachim Siedel, Bernried; Hans Möllering, Tutzing; Hans Seidel, Tutzing; Helmgard Gauhl, Tutzing, all of Fed. Rep. of Germany

[73] Assignee: Boehringer Mannheim GmbH, Mannheim-Waldhof, Fed. Rep. of Germany

[21] Appl. No.: 328,312

[22] Filed: Dec. 7, 1981

[30] Foreign Application Priority Data

Dec. 11, 1980 [DE] Fed. Rep. of Germany ....... 3046741

[51] Int. Cl.$^3$ .... C12Q 1/38; C12Q 1/40; C12Q 1/14; C12Q 1/54; C12Q 1/56; C12N 9/02
[52] U.S. Cl. ........................................ 435/25; 435/14; 435/13; 435/19; 435/22; 435/23; 435/26; 435/189; 435/805; 435/810
[58] Field of Search ................... 435/4, 14, 13, 19, 22, 435/23, 25, 26, 805, 810, 190, 192, 189

[56] References Cited

U.S. PATENT DOCUMENTS 4,168,205  9/1979  Danninger et al. ................... 435/14

OTHER PUBLICATIONS

White-Stevens et al., J. Biol. Chem., 247(8), 2358-2370 (1972).
Dawson et al. *Methods in Enzymology*, vol. II, Academic Press, Inc., New York, 817-828 (1955).

*Primary Examiner*—Esther M. Kepplinger
*Attorney, Agent, or Firm*—Felfe & Lynch

[57] ABSTRACT

The present invention provides a process for the determination of NAD(P)H or of salicylate, wherein, in a NAD(P)H-dependent reaction, salicylate is decarboxylated by salicylate hydroxylase and a colored material is formed from the decarboxylation product in the presence of tyrosinase by oxidative coupling with an appropriate colored material component, the colored material formed then being determined photometrically.

The present invention also provides a reagent for the determination of NADH or NADPH, wherein it contains salicylate, a chromogenic hydrazone or amine, salicylate hydroxylase, tyrosinase and buffer, as well as a reagent for the determination of salicylate, wherein it contains NAD(P)H, a chromogenic hydrazone or amine, salicylate hydroxylase, tyrosinase and buffer.

8 Claims, No Drawings

DETERMINATION OF NAD(P)H OR SALICYLATE

This invention relates to a method for the detection of NAD(P)H or NAD(P)H-forming enzyme reactions or of salicylate or salicylate-yielding enzyme reactions. In additional aspect the invention relates to a reagent for determining NADH or NADPH or salicylate.

The determination of diagnostic parameters, such as glucose or glycerol, is of great importance in clinical chemistry, dehydrogenases or oxidases usually being employed for this purpose.

Oxidases are preferably employed since the resultant hydrogen peroxide can be detected by a colour reaction in which, for example, in the presence of peroxidase, chromogens are oxidatively coupled by the action of hydrogen peroxide to give a coloured material. Such systems have the advantage that the reagents used for the determination are stable and offer the possibility, by suitable choice of the coupling component, so to influence the extinction maximum and wavelength that they can be measured free of disturbance.

However, this method also suffers from serious disadvantages: thus, oxidases are relatively nonspecific enzymes so that the presence of other oxidisable substances in the test batch can prove to be disturbing. Furthermore, the intermediate product, hydrogen peroxide, is frequently not formed stoichiometrically and, in addition, is very unstable. The reaction of the hydrogen peroxide formed by peroxidase proceeds stoichiometrically unfavourably: at least 2 moles of hydrogen peroxide are required per mole of resultant coloured material.

In contradistinction thereto, dehydrogenase reactions proceed strictly stoichiometrically and, in general, also substantially more specifically than oxidase reactions. Furthermore, the intermediate product NAD(P)H is very stable.

Therefore, it would be desirable to be able to combine the advantages of the specific and stoichiometric dehydrogenase reaction with the advantages of a coloured material-forming reaction.

It is known that the reaction product NAD(P)H can be converted in a dehydrogenase reaction by means of diaphorase and tetrazolium salts into a coloured material. However, this system also presents great difficulties since tetrazolium salts are unstable and the coloured material formed tends to polymerise and thus to become insoluble.

Therefore, it is an object of the present invention to provide a process for making NAD(P)H visible, which does not display these disadvantages and also satisfies the need for a method for the determination of salicylate.

Thus, according to the present invention, there is provided a process for the determination of NAD(P)H or of salicylate, wherein, in a NAD(P)H-dependent reaction, salicylate is decarboxylated by salicylate hydroxylase and a coloured material is formed from the decarboxylation product in the presence of tyrosinase by oxidative coupling with an appropriate coloured material component, the coloured material formed then being determined photometrically.

The following known reactions provide the basis for the process according to the present invention:

salicylate + NAD(P)H +  (1)

$O_2$ <u>salicylate hydroxylase (EC 1.14.13.1)</u> → pyrocatechol + $CO_2$ + $H_2O$ + $NAD^+$ pyrocatechol + hydrazone + (2)

$O_2$ <u>tyrosinase (EC 1.10.3.1) or (EC 1.14.18.1)</u> → acine coloured material + $H_2O$

Reaction (1) is known from R. H. White-Stevens and H. Kamin, J. biol. Chem., 247, 2358/1972. By salicylate, there is to be understood not only salicylate per se but also all salicylate derivatives.

Of reaction (2), it is known that tyrosinase, apart from pyrocatechol, also oxidises monophenols and oxidatively couples hydrazones on to the thereby resulting quinones to give coloured materials (C. R. Dawson and R. J. Magee, Methods in Enzymology, 2, 817/1955; B. G. Malmstrom and L. Ryden, Biological Oxidations (ed. T. P. Singer), p. 419, pub. Interscience Publ. New York/1968). Therefore, it was not to have been expected that a coupling of reactions (1) and (2) could be used as an indicator system for NAD(P)H since a disturbance by the direct reaction of salicylate with the hydrazone in the presence of tyrosinase was to have been expected.

Surprisingly, however, we have found that tyrosinase does not react with salicylate and only oxidatively couples the reaction product pyrocatechol under the conditions of the test. This reaction takes place stoichiometrically, 1 mole of a stable coloured material complex resulting per mole of pyrocatechol.

The present invention can be broadly used for all NADH- or NADPH-forming reactions. Examples of NAD(P)H-forming reactions include the determination of substrates such as glucose, glucose-6-phosphate, glycerol and triglycerides with the help of various dehydrogenases. The determination of enzyme activities of various dehydrogenases, for example of glucose-6-phosphate dehydrogenase, is also possible. From the reactions forming the basis of the process, there is, at the same time, also obtained the possibility of using the present invention for the determination of salicylate or of salicylate derivatives when NAD(P)H is present in the reaction mixture in excess in comparison with the salicylate to be determined. All salicylate-forming reactions can be determined in this way. One possibility is, for example, the determination of hydrolases which are able to split compounds of the general formulae:

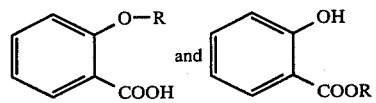

including proteases, coagulation factors, amylase and lipase.

The coloured material-forming component can be a hydrazone or amine.

By the selection of various couplable hydrazones or amines, the extinction and wavelength can be influenced as desired. Appropriate compounds include, for example, all the hydrazones which have been described by S. Hunig in Angewandte Chemie, 70, 215/1958. In a preferred embodiment, 3-methylbenzothiazol-2-one hydrazone 6-sulphonic acid (MBTH-S) is used as the couplable hydrazone:

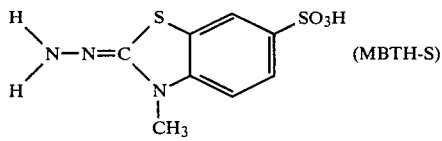

(MBTH-S)

The chromogenic amine used can be, for example, proline, protamine, histamine and lysine.

The present invention also provides a reagent for the determination of NADH or NADPH which contains salicylate, a chromogenic hydrazone or amine, salicylate hydroxylase, tyrosinase and buffer; and a reagent for the determination of salicylate, which contains NAD(P)H, chromogenic hydrazone or amine, salicylate hydroxylase, tyrosinase and buffer. Apart from the mentioned obligatory components, the reagent combination can also contain additional conventional solvents and adjuvants, for example, stabilisers and surface-active substances.

All buffers can be used which buffer in a pH range of from 6 to 9.3, with a buffer strength of 0.005 to 1.0 mole/liter, phosphate and glycylglycine buffers being preferred. The enzymes are preferablyused in the following concentrations: salicylate hydroxylase 0.05 to 5.0 kU/liter and tyrosinase 10 to 200 kU/liter. The reagent according to the present invention can be impregnated on to carriers, for example, papers, synthetic resin films or other porous bodies and thus, for example, be used as test strips.

The following Examples are given for the purpose of illustrating the present invention:

EXAMPLE 1

NADH determination

The reagent consists of:
MBTH-S—1.7 mmol/liter
SAHX—70 U/liter
tyrosinase—33×10³ U/liter
sodium salicylate—0.33 mmol/liter
potassium phosphate buffer (pH 7.0)—0.1 mol/liter
Start of the reaction: addition of the NADH-containing sample. Measurement at 492 nm, 25° C. End point: after 15 minutes for 0.02 μmole NADH in 3 ml. test volume.

EXAMPLE 2

NADPH determination

Analogous to Example 1.
Start of the reaction: addition of the NADPH-containing sample.

EXAMPLE 3

Determination of glucose-6-phosphate

The reagent consists of:

| | |
|---|---|
| MBTH-S | ⎫ |
| SAHX | ⎬ as in |
| tyrosinase | ⎬ Example 1 |
| sodium salicylate | ⎭ |
| potassium phosphate buffer (pH 7.0) | |
| glucose-6-phosphate dehydrogenase (Leuconostoc mesenteroides) | 1.6 × 10³ U/liter |
| NAD+ | 0.25 mmol/liter |

Start of the reaction: with sample. Measurement at 492 nm, 25° C. End point of the reaction: 5 minutes.

EXAMPLE 4

Determination of the activity of glucose-6-phosphate dehydrogenase

The reagent consists of:

| | |
|---|---|
| MBTH-S | ⎫ |
| SAHX | ⎬ |
| tyrosinase | ⎬ as in |
| sodium salicylate | ⎬ Example 1 |
| potassium phosphate buffer (pH 7.0) | ⎭ |
| NAD+ | 0.25 mmol/liter |
| glucose-6-phosphate | 3.3 mmole/liter |

Start: with the G-6-PDH-containing sample.
Measurement at 492 nm, 25° C.

EXAMPLE 5

Glycerol determination

The reagent consists of:
MBTH-S—1.7 mmol/liter
SAHX—80 U/liter
tyrosinase—66×10³ U/liter
glycerol dehydrogenase—2400 U/liter
sodium salicylate—0.33 mmol/liter
NAD+—1.35 mmol/liter
glycylglycine buffer (pH 8.5)—0.1 mol/liter
ammonium sulphate—0.01 mol/liter
Start: by addition of the sample. Measurement: 492 nm, 25° C. End point: after 30 minutes.

EXAMPLE 6

Determination of triglycerides

The reagent consists of:

| | |
|---|---|
| MBTH-S | ⎫ |
| SAHX | ⎬ |
| tyrosinase | ⎬ |
| glycerol dehydrogenase | ⎬ as in Example 5 |
| sodium salicylate | ⎬ |
| NAD+ | ⎬ |
| glycylglycine buffer (pH 8.5) | ⎭ |
| ammonium sulphate | |
| esterase from Pseudomonas | 1000 U/liter |
| isotridecyl ether | 2 g./liter |

Measurement: 492 nm, 25° C. End point: after 30 minutes.

EXAMPLE 7

Determination of salicylic acid

The reagent consists of:
MBTH-S—1.7 mmol/liter
SAHX—70 U/liter
tyrosinase—33×10³ U/liter
NADH—0.23 mmol/liter
potassium phosphate buffer (pH 7.0)—0.1 mol/liter
Start: by addition of the sample. Measurement: 492 nm, 25° C. End point: after 10 minutes for 0.02 μmole salicylate in a test volume of 3 ml.

In Examples 1 to 7, the 1.7 mmol/liter of MBTH-S can, in each case, be replaced by 10 mmol/liter proline, without the results being changed. In this case, the measurement is carried out at 546 nm.

It will be understood that the specification and examples are illustrative but not limitative of the present invention and that other embodiments within the spirit and scope of the invention will suggest themselves to those skilled in the art.

What is claimed is:

1. Method for the determination of NAD(P)H or of salicylate comprising;
   (a) decarboxylating salicylate by use of salicylate hydroxylase in a NAD(P)H dependent reaction in the presence of tyrosinase and of an appropriate chromogenic component selected from the group consisting of hydrazones and amines to form a colored material by oxidative coupling of the decarboxylation product with the said chromogenic component; and
   (b) determining the colored material formed photometrically.

2. Method as claimed in claim 1, wherein NAD(P)H is determined.

3. Method as claimed in claim 1, wherein salicylate is determined.

4. Reagent for the determination of NADH comprising salicylate, a chromogenic hydrazone or amine, salicylate hydroxylase, tyrosinase and a buffer.

5. Reagent for the determination of salicylate, comprising NAD(P)H, a chromogenic hydrazone or amine, salicylate hydroxylase, tyrosinase and buffer.

6. Reagent as claimed in claim 4 comprising:
   0.05 to 20 mmol/liter salicylate,
   0.3 to 30 mmol/liter hydrazone or amine,
   0.05 to 5 kU/liter salicylate hydroxylase,
   10 to 200 kU/liter tyrosinase and buffer (pH 6.0 to 9.3).

7. Reagent as claimed in claim 5 comprising:
   0.05 to 1.5 mmol/liter NAD(P)H,
   0.3 to 30 mmol/liter hydrazone or amine,
   0.05 to 5 kU/liter salicylate hydroxylase,
   10 to 200 kU/liter tyrosinase and buffer (pH 6.0 to 9.3).

8. Reagent as claimed in claim 4, wherein the hydrazone is 3-methyl-benzothiazol-2-one hydrazone 6-sulfonic acid (MBTH-S).

* * * * *